(12) United States Patent
Heathman et al.

(10) Patent No.: US 7,621,186 B2
(45) Date of Patent: Nov. 24, 2009

(54) TESTING MECHANICAL PROPERTIES

(75) Inventors: James Heathman, Harris, TX (US);
Dennis Gray, Comanche, OK (US); Joe Maxson, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 43 days.

(21) Appl. No.: 11/669,771

(22) Filed: Jan. 31, 2007

(65) Prior Publication Data

US 2008/0178683 A1    Jul. 31, 2008

(51) Int. Cl.
*G01N 3/00*    (2006.01)
(52) U.S. Cl. .................................................. 73/803
(58) Field of Classification Search ................ 73/803, 73/865.6
See application file for complete search history.

(56) References Cited

U.S. PATENT DOCUMENTS

| | | | |
|---|---|---|---|
| 2,662,827 A | | 12/1953 | Clark |
| 3,541,845 A | * | 11/1970 | Kierkegaard-Hansen ..... 73/803 |
| 3,574,281 A | | 4/1971 | Casey et al. |
| 3,619,463 A | | 11/1971 | Budin et al. |
| 3,779,085 A | | 12/1973 | Rice |
| 4,138,892 A | * | 2/1979 | Davis ........................ 73/866.4 |
| 4,259,868 A | | 4/1981 | Rao et al. |
| 4,377,087 A | | 3/1983 | Rodot |
| 4,389,896 A | | 6/1983 | Babcock |
| 4,408,489 A | | 10/1983 | Spangle |
| 4,430,889 A | | 2/1984 | Sutton |
| 4,487,056 A | | 12/1984 | Wiley |
| 4,491,017 A | | 1/1985 | Iyler |
| 4,538,452 A | | 9/1985 | Hrvojic |
| 4,567,759 A | | 2/1986 | Ekstrom et al. |
| 4,567,765 A | | 2/1986 | Rao et al. |
| 4,607,530 A | | 8/1986 | Chow |

(Continued)

FOREIGN PATENT DOCUMENTS

DE    86 01 833    1/1987

(Continued)

OTHER PUBLICATIONS

Dillenbeck, R.L., GoBoncan, V., and Rogers, M.J., "*Testing Cement Static Tensile Behavior Under Downhole Conditions*," SPE 97967, Society of Petroleum Engineers, Copyright 2005, 12 pages.

(Continued)

*Primary Examiner*—Lisa M Caputo
*Assistant Examiner*—Freddie Kirkland, III
(74) *Attorney, Agent, or Firm*—John W. Wustenberg; Fish & Richardson P.C.

(57) ABSTRACT

Cement is conditioned, cured and/or tested while applying a specified temperature and/or pressure. In certain embodiments, the specified temperature and/or pressure applied during the testing substantially simulates anticipated static downhole conditions the cement will be subjected to in use. In certain embodiments, the specified temperature and/or pressure applied during the receiving substantially simulates pumping placement conditions the cement will be subjected to in use. In certain embodiments, the cement can be conditioned in a conditioning vessel while applying specified temperature and/or pressure to the cement. In certain embodiments, the temperature and/or pressure applied in the conditioning substantially simulates anticipated pumping placement conditions the cement will be subjected to in use.

23 Claims, 3 Drawing Sheets

U.S. PATENT DOCUMENTS

| | | | |
|---|---|---|---|
| 4,648,264 A * | 3/1987 | Freese et al. | 73/64.41 |
| 4,685,092 A | 8/1987 | Dumont | |
| 4,691,558 A | 9/1987 | Vinson et al. | |
| 4,703,427 A | 10/1987 | Catala et al. | |
| 4,757,479 A | 7/1988 | Masson et al. | |
| 4,809,237 A | 2/1989 | Vogel et al. | |
| 4,823,594 A | 4/1989 | Gray | |
| 4,848,145 A | 7/1989 | Blaschke et al. | |
| 4,893,285 A | 1/1990 | Masson et al. | |
| 4,896,303 A | 1/1990 | Leslie et al. | |
| 4,970,695 A | 11/1990 | Huau | |
| 5,009,512 A * | 4/1991 | Lessi et al. | 374/6 |
| 5,036,709 A * | 8/1991 | McRae | 73/841 |
| 5,089,989 A | 2/1992 | Schmidt et al. | |
| 5,127,473 A | 7/1992 | Harris et al. | |
| 5,216,638 A | 6/1993 | Wright | |
| 5,233,863 A | 8/1993 | Surjaatmadja et al. | |
| 5,248,200 A * | 9/1993 | Walsh | 374/45 |
| 5,325,723 A | 7/1994 | Meadows et al. | |
| 5,346,012 A | 9/1994 | Heathman et al. | |
| 5,353,637 A | 10/1994 | Plumb et al. | |
| 5,368,103 A | 11/1994 | Heathman et al. | |
| 5,377,160 A | 12/1994 | Tello et al. | |
| 5,377,753 A | 1/1995 | Haberman et al. | |
| 5,389,706 A | 2/1995 | Heathman et al. | |
| 5,412,990 A | 5/1995 | D'Angelo et al. | |
| 5,487,307 A | 1/1996 | Landgren et al. | |
| 5,488,994 A | 2/1996 | Laurel et al. | |
| 5,544,704 A | 8/1996 | Laurel et al. | |
| 5,571,951 A * | 11/1996 | Jamth | 73/54.03 |
| 5,572,021 A | 11/1996 | Heathman et al. | |
| 5,696,059 A | 12/1997 | Onan et al. | |
| 5,712,431 A * | 1/1998 | Vilendrer | 73/841 |
| 5,718,292 A | 2/1998 | Heathman et al. | |
| 5,741,971 A | 4/1998 | Lacy | |
| 5,763,773 A | 6/1998 | Birchak et al. | |
| 5,783,822 A | 7/1998 | Buchanan et al. | |
| 5,787,983 A | 8/1998 | Heathman et al. | |
| 5,836,200 A | 11/1998 | Belonenko et al. | |
| 5,869,750 A | 2/1999 | Onan et al. | |
| 5,964,293 A | 10/1999 | Chatterji et al. | |
| 5,968,255 A | 10/1999 | Mehta et al. | |
| 5,969,059 A | 10/1999 | Murai et al. | |
| 5,972,103 A | 10/1999 | Mehta et al. | |
| 5,992,223 A | 11/1999 | Sabrins et al. | |
| 5,996,693 A | 12/1999 | Heathman | |
| 6,019,835 A | 2/2000 | Chatterji et al. | |
| 6,053,245 A | 4/2000 | Haberman | |
| 6,055,874 A | 5/2000 | Onan et al. | |
| 6,060,434 A | 5/2000 | Sweatman et al. | |
| 6,070,662 A | 6/2000 | Ciglenec et al. | |
| 6,112,599 A | 9/2000 | Maki, Jr. | |
| 6,124,246 A | 9/2000 | Heathman et al. | |
| H1932 H | 1/2001 | Heathman et al. | |
| 6,170,575 B1 | 1/2001 | Reddy et al. | |
| 6,209,646 B1 | 4/2001 | Reddy et al. | |
| 6,227,039 B1 | 5/2001 | Te'eni | |
| 6,227,294 B1 | 5/2001 | Chatterji et al. | |
| 6,245,142 B1 | 6/2001 | Reddy et al. | |
| 6,258,757 B1 | 7/2001 | Sweatman et al. | |
| 6,269,684 B1 | 8/2001 | Maki, Jr. et al. | |
| 6,270,565 B1 | 8/2001 | Heathman | |
| 6,345,535 B1 | 2/2002 | Sabins et al. | |
| 6,367,549 B1 | 4/2002 | Chatterji et al. | |
| 6,367,550 B1 | 4/2002 | Chatterji et al. | |
| 6,379,456 B1 | 4/2002 | Heathman et al. | |
| 6,444,316 B1 | 9/2002 | Reddy et al. | |
| 6,454,001 B1 | 9/2002 | Thompson et al. | |
| 6,478,868 B1 | 11/2002 | Reddy et al. | |
| 6,478,869 B2 | 11/2002 | Reddy et al. | |
| 6,484,568 B1 | 11/2002 | Griffith et al. | |
| 6,494,951 B1 | 12/2002 | Reddy et al. | |
| 6,510,743 B2 * | 1/2003 | McAfee et al. | 73/803 |
| 6,527,051 B1 | 3/2003 | Reddy et al. | |
| 6,527,438 B2 | 3/2003 | Zollinger et al. | |
| 6,547,871 B2 | 4/2003 | Chatterji et al. | |
| 6,554,071 B1 | 4/2003 | Crook et al. | |
| 6,591,910 B1 | 7/2003 | Chatterji et al. | |
| 6,595,068 B2 | 7/2003 | Brovold et al. | |
| 6,610,139 B2 | 8/2003 | Crook et al. | |
| 6,644,402 B1 | 11/2003 | Sharma et al. | |
| 6,655,213 B1 | 12/2003 | Reinhardt et al. | |
| 6,660,080 B2 | 12/2003 | Reddy et al. | |
| 6,762,156 B2 | 7/2004 | Heathman et al. | |
| 6,767,867 B2 | 7/2004 | Chatterji et al. | |
| 6,782,735 B2 | 8/2004 | Walters et al. | |
| 6,789,621 B2 | 9/2004 | Wetzel et al. | |
| 6,797,054 B2 | 9/2004 | Chatterji et al. | |
| 6,817,238 B2 | 11/2004 | Go Boncan et al. | |
| 6,818,596 B1 | 11/2004 | Hayes | |
| 6,828,922 B1 | 12/2004 | Gremmert et al. | |
| 6,829,922 B2 | 12/2004 | Patin et al. | |
| 6,834,233 B2 | 12/2004 | Economides et al. | |
| 6,843,846 B2 | 1/2005 | Chatterji et al. | |
| 6,874,353 B2 | 4/2005 | Johnson et al. | |
| 6,892,814 B2 | 5/2005 | Heathman et al. | |
| 6,910,535 B2 | 6/2005 | Tare et al. | |
| 6,918,292 B2 | 7/2005 | Go Boncan et al. | |
| 6,951,249 B1 | 10/2005 | Chatterji et al. | |
| 6,964,302 B2 | 11/2005 | Luke et al. | |
| 6,978,835 B1 | 12/2005 | Reddy et al. | |
| 6,994,164 B2 | 2/2006 | Tare et al. | |
| 7,004,256 B1 | 2/2006 | Chatterji et al. | |
| 7,008,477 B2 | 3/2006 | Chatterji et al. | |
| 7,013,975 B2 | 3/2006 | Chatterji et al. | |
| 7,048,054 B2 | 5/2006 | Heathman et al. | |
| 7,089,816 B2 * | 8/2006 | Hakimuddin | 73/866 |
| 7,096,944 B2 | 8/2006 | Vargo, Jr. et al. | |
| 7,128,142 B2 | 10/2006 | Heathman et al. | |
| 7,128,149 B2 | 10/2006 | Heathman et al. | |
| 7,143,827 B2 | 12/2006 | Chatterji et al. | |
| 7,178,590 B2 | 2/2007 | Vargo, Jr. et al. | |
| 7,240,545 B1 | 7/2007 | Jennings | |
| 7,244,303 B2 | 7/2007 | Chatterji et al. | |
| 7,255,170 B2 | 8/2007 | Chatterji et al. | |
| 7,284,898 B2 | 10/2007 | Duell et al. | |
| 7,285,166 B2 | 10/2007 | Luke et al. | |
| 7,296,927 B2 * | 11/2007 | Reddy et al. | 374/47 |
| 7,325,629 B2 | 2/2008 | Blaschke et al. | |
| 7,373,982 B2 | 5/2008 | Brothers et al. | |
| 7,380,466 B2 * | 6/2008 | Deeg | 73/803 |
| 2001/0001381 A1 | 5/2001 | Reddy et al. | |
| 2001/0037687 A1 | 11/2001 | Brovold et al. | |
| 2003/0140707 A1 | 7/2003 | Pyle et al. | |
| 2003/0150263 A1 | 8/2003 | Economides et al. | |
| 2003/0161211 A1 | 8/2003 | Duell et al. | |
| 2003/0221829 A1 | 12/2003 | Patel et al. | |
| 2004/0054262 A1 | 3/2004 | Horak | |
| 2004/0055392 A1 | 3/2004 | Patin et al. | |
| 2004/0154263 A1 | 8/2004 | Li et al. | |
| 2004/0221990 A1 | 11/2004 | Heathman et al. | |
| 2004/0226483 A1 | 11/2004 | Chatterji et al. | |
| 2005/0009710 A1 | 1/2005 | Heathman et al. | |
| 2005/0080161 A1 | 4/2005 | Tare et al. | |
| 2005/0109507 A1 | 5/2005 | Heathman et al. | |
| 2005/0126300 A1 * | 6/2005 | Go Boncan et al. | 73/803 |
| 2005/0135185 A1 | 6/2005 | Duell et al. | |
| 2005/0152432 A1 * | 7/2005 | Hakimuddin | 374/53 |
| 2005/0204960 A1 | 9/2005 | Heathman et al. | |
| 2006/0000612 A1 | 1/2006 | Reddy et al. | |
| 2006/0225523 A1 * | 10/2006 | Reddy et al. | 73/865.6 |
| 2006/0258545 A1 | 11/2006 | Chatterji et al. | |
| 2007/0012441 A1 | 1/2007 | Heathman et al. | |
| 2007/0082822 A1 | 4/2007 | Kirsner et al. | |

| | | | |
|---|---|---|---|
| 2007/0105995 | A1 | 5/2007 | Chatterji et al. |
| 2007/0169937 | A1 | 7/2007 | Allin et al. |
| 2007/0173412 | A1 | 7/2007 | Allin et al. |
| 2008/0168848 | A1 | 7/2008 | Funkhouser et al. |
| 2008/0197605 | A1 | 8/2008 | Blaschke et al. |

FOREIGN PATENT DOCUMENTS

| | | |
|---|---|---|
| EP | 0 124 383 A1 | 11/1984 |
| EP | 0 176 400 B1 | 4/1986 |
| EP | 0 176 408 B1 | 4/1986 |
| EP | 0 101 580 B1 | 12/1986 |
| EP | 0 110 750 B1 | 9/1988 |
| EP | 0 098 778 B1 | 3/1989 |
| EP | 0 198 985 B1 | 12/1989 |
| EP | 0 443 936 A1 | 8/1991 |
| EP | 0 395 499 B1 | 7/1993 |
| EP | 0 865 612 B1 | 6/2002 |
| EP | 1 541 987 | 6/2005 |
| GB | 2 353 546 A | 2/2001 |
| GB | 2 354 026 A | 3/2001 |
| GB | 2 355 742 A | 5/2001 |
| GB | 2 386 625 A | 9/2003 |
| WO | WO 00/49273 | 8/2000 |
| WO | WO 2004/008302 | 10/2004 |
| WO | WO 2005/065411 | 7/2005 |

OTHER PUBLICATIONS

Minear, John W. and Goodwin, K. Joe, "*Cement-Sheath Evaluation*," Chapter 10, Petroleum Well Construction, John Wiley & Sons Publisher, ISBN 0-471-96938-9, copyright 1998, front and back cover and pp. 271-296.

Love, A.E.H., "*A Treatise on the Mathematical Theory of Elasticity*," Fourth Edition, Dover Publications, New York, 1944, pp. 144-145.

Thiercelin, J.J., et al., "*Cement Design Based on Cement Mechanical Response*," SPE Drilling & Completion, Dec. 1998, pp. 266-273.

Goodwin, K.J., "*Cement Sheath Stress Failure*," SPE Drilling Engineering, SPE 20453, Dec. 1992, pp. 291-296, and additional pp. 501-508 from SPE 20453.

Deeg, Wolfgang, et al., "*How Foamed Cement Advantages Extend to Hydraulic Fracturing Operations*," World Oil, Nov. 1999, pp. 51-53.

FlexiForce®, materials downloaded from Tekscan website (www.tekscan.com) on FlexiForce® sensors), http://www.tekscan.com/flexiforce.html, visited Aug. 3, 2005, 20 pages.

Bridgman, P. W., "V. Breaking Tests Under Hydrostatic Pressure and Conditions of Rupture", *Philosophical Magazine and Journal of Science*, vol. 24, Sixth Series, pp. 63-80, (1912).

Clayton, N., "Fluid-pressure Testing of Concrete Cylinders," *Magazine of Concrete Research*, vol. 30, No. 102, pp. 26-30, (1978).

Clayton, N. et al., "The Diphase Concept, With Particular Reference to Concrete", *Developments in Concrete Technology*, vol. 1, F. D. Lydon, Ed.; Applied Science Publisher Ltd, Chapter 7, pp. 283-318, (1979).

Richart, Frank E. et al., "A Study of the Failure of Concrete Under Combined Compressive Stresses", The University of Illinois—Engineering Experiment Station, Bulletin No. 185, pp. 3-253, (1928).

Mindess, S. et al., "The Nitrogen Gas Tension Test of Concrete", Proceedings of ConMat '05 and Mindess Symposium, Aug. 22-24, 2005, The University of British Columbia, Vancouver, Canada, 8 pages, (2005).

Joyce, David, "International Search Report" PCT/GB2006/003052, mailed Dec. 21, 2006, 2 pages.

Timonen, Tuomo, "International Search Report" PCT/GB2008/000031, mailed Apr. 2, 2008, 3 pages.

"Standard Test Method for Tensile Strength of Hydraulic Cement Mortars", ASTM Standards, C 190-85, pp. 197-202.

Sabins, Fred, "MMS Project Long Term Integrity of Deepwater Cement Systems Under Stress/Compaction Conditions", CSI Technologies, Sep. 3, 2004.

* cited by examiner

TESTING MECHANICAL PROPERTIES

BACKGROUND

This disclosure relates to evaluating cement formulations for use in subterranean cementing operations.

Some well bores, for example those of some oil and gas wells, are lined with a casing. The casing stabilizes the sides of the well bore, prevents fluids (liquids or gasses) in the well bore from entering the surrounding earth formations, and/or prevents fluids from zones other than the producing zones from entering the well bore.

In a cementing operation, cement is introduced down the well bore and into an annular space between the casing and the surrounding earth. The cement secures the casing in the well bore, and prevents fluids from flowing vertically in the annulus between the casing and the surrounding earth.

Cement formulations can be designed for specific well bore conditions, which may be above or below ambient temperature and pressure. In designing a cement formulation, a number of potential mixtures may be evaluated to determine their mechanical properties under various conditions.

SUMMARY

The disclosure herein encompasses systems and methods for conditioning, curing and/or testing one or more mechanical properties of cement while applying specified temperatures and/or pressures.

One aspect encompasses a method of testing a mechanical property of a cement. In the method, the cement is conditioned in a conditioning vessel. The cement is then received in a testing vessel and cured, and a mechanical property of the cement is tested in the testing vessel. The cement is conditioned, cured and tested while applying a specified temperature and/or pressure. In certain embodiments, the specified temperature and/or pressure applied during the testing substantially simulates anticipated static downhole conditions the cement will be subjected to in use. In certain embodiments, the specified temperature and/or pressure applied during the receiving substantially simulates pumping placement conditions the cement will be subjected to in use. In certain embodiments, the cement can be conditioned in a conditioning vessel while applying specified temperature and/or pressure to the cement. In certain embodiments, the temperature and/or pressure applied in the conditioning substantially simulates anticipated pumping placement conditions the cement will be subjected to in use. Of note, the specified temperature and/or pressure need not be applied during every operation (conditioning, curing and testing) and need not be applied throughout the duration each operation.

Another aspect encompasses a system for testing cement. The system includes a testing vessel having interior walls defining a mold cavity to receive the cement. A body is in the mold cavity that is adapted to apply a specified pressure to the cement while it is being received in the mold cavity. In certain embodiments, the interior walls define at least a portion of the mold cavity as frustoconical. In certain embodiments, the interior walls further define at least a portion of the mold cavity as cylindrical. In certain embodiments, a load arm is included and adapted to contact the cement and apply a testing load to the cement, and the interior walls of the testing vessel are configured to anchor the cement against the testing loads. In certain embodiments, the load arm is operable to load the cement in tension until failure at a break area and the testing vessel is adapted to mold the cement in an annular shape about the break area. In certain embodiments, the load arm is operable to load the cement in tension until failure at a break area, as well as shear the bond between the cement and a wall of the testing vessel.

Yet another aspect encompasses a method where the cement is received in a testing vessel, and the cement cures in the vessel. A mechanical property of the cement is tested in the testing vessel. In the method, the cement is received in the testing vessel, cured and tested while applying specified temperature and/or pressure to the cement. In certain embodiments, the specified temperature and/or pressure applied while curing and testing substantially simulates anticipated static downhole conditions the cement will be subjected to in use. In certain embodiments, the specified temperature and/or pressure applied while receiving substantially simulates anticipated pumping placement downhole conditions the cement will be subjected to in use.

Yet another aspect encompasses a method where a cement is received in a testing vessel, and cures in the testing vessel. A shear bond strength of the cement is tested. In the method the cement is cured and tested while applying a specified temperature and/or pressure. In certain embodiments, the specified temperature and/or pressure applied while curing and testing substantially simulates anticipated static downhole conditions the cement will be subjected to in use.

In some implementations, both tensile load tests and shear bond tests can be performed on the same sample.

Other variations will be apparent from the following drawings and detailed description.

DESCRIPTION OF DRAWINGS

Like reference symbols in the various drawings indicate like elements.

DETAILED DESCRIPTION

Certain of the devices and methods described herein enable measurement of mechanical properties and behaviors of cement formulations while simulating the anticipated conditions the cement will be subjected to in use. For example, certain of the devices and methods described herein enable the cement to be cured at anticipated static well bore conditions and the mechanical properties tested at static well bore conditions. Certain of the devices and methods described herein also enable the cement to be mixed and/or conditioned at the anticipated pumping placement conditions. Certain of the devices and methods described herein also enable mixing and/or conditioning, curing, and/or measurement of mechanical properties and behaviors of cement formulations at other specified conditions. Furthermore, the devices can be so configured to form the cement being tested into shapes that facilitate the testing. In certain embodiments, the mechanical properties that can be tested include one or more of tensile strength, shear bond strength. Young's modulus, Poisson's ratio, and other properties.

As used herein, "cement" and "cement formulation" encompass a fluid mixture that hardens into solid, and may be any agent suitable to bond casing or other tubulars to well bore walls or to other tubing used for downhole applications. Some examples of cement include hydraulic cement (e.g.

Portland cement formulations) and non-hydraulic cement (e.g. polymer resin formulations). As used herein, "curing" refers to the reactions through which a cement hardens from a fluid mixture into a solid. "Cured" is cement that has solidified.

Figure 1:
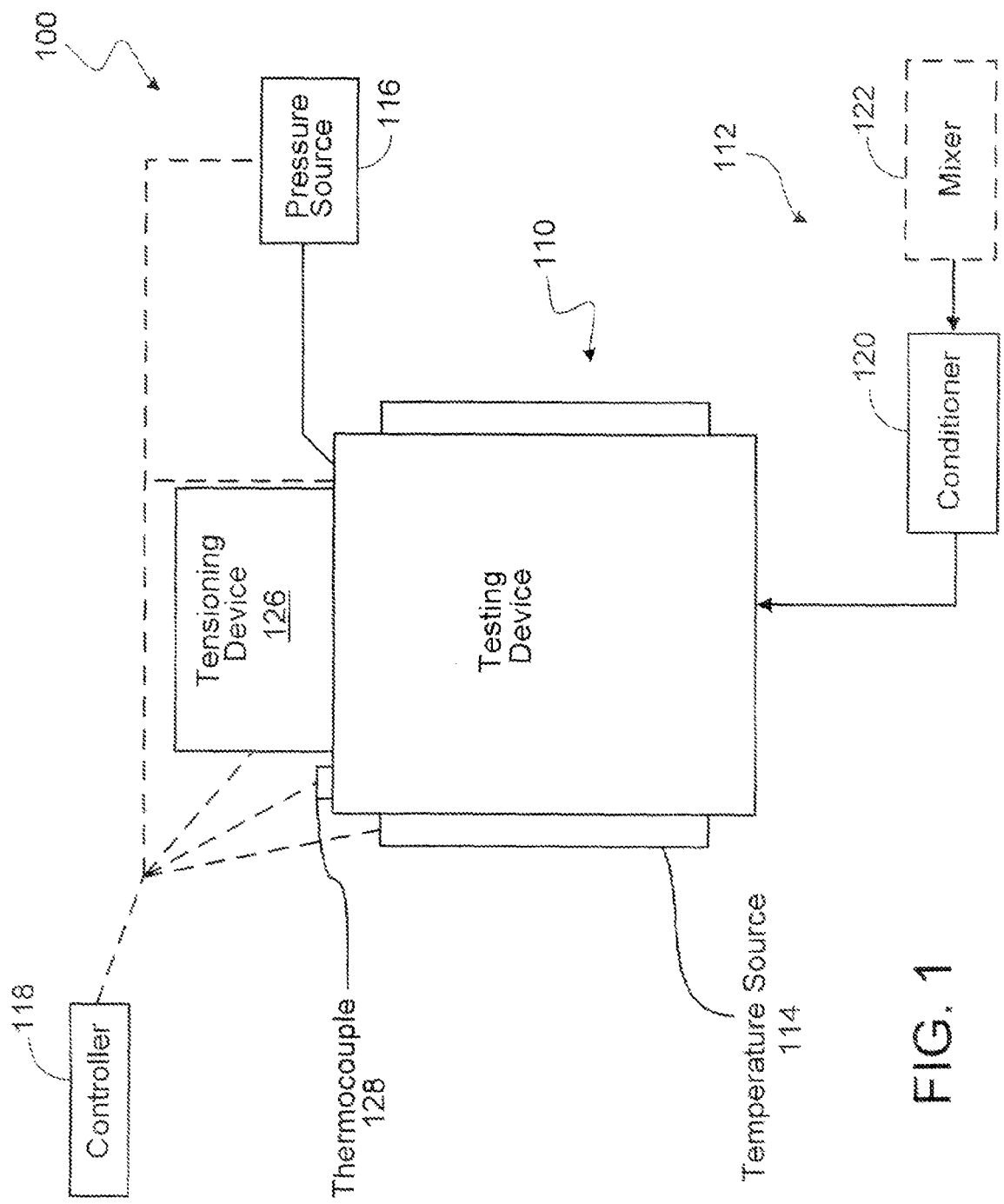
FIG. 1 is a schematic view of one embodiment of a system for evaluating mechanical properties of a cement formulation.

Referring to FIG. 1, an example system 100 for measuring mechanical properties of cement includes a testing device 110, a cement source 112, a temperature source 114, a pressure source 116, a controller 118, a conditioner 120 and, in some instances, a mixer 122. Cement source 112 can provide flowable cement to testing device 110 for testing. In some instances, cement source 112 can include a conditioner 120 adapted to apply specified pressures (e.g. via a piston, pump or other) and/or temperatures (e.g. via a heating element, heat exchanger or other) to the cement before it is introduced into testing device 110. In certain embodiments, the conditioner 120 may be a consistometer for measuring cement viscosity and changes in viscosity over time at ambient or specified temperature and/or pressure. The cement formulation may be partially or completely mixed in the conditioner 120 or in an optional mixer 122 at ambient or specified temperature and/or pressure. In either instance, mixing involves agitating, by stirring, vibrating, folding or other, the constituents of the cement (e.g. Portland cement powder, additives and liquid, polymer, additives and catalyst, or other formulations of constituents) together to form cement. Mixing is complete when no further mixing will be performed on the cement before testing.

Testing device 110 can include a test vessel 124, a tensioning device 126, and thermocouple 128. The interior walls of the test vessel 124 define an interior mold cavity 154 that acts as a mold to mold the cement into a specified shape. In certain embodiments, the shape can facilitate testing, for example, by simulating the shape of the cement during use. In some embodiments, the test vessel 124 is a pressure vessel configured to hold specified pressures above or below ambient. As such, the cement can be cured or partially cured at specified pressures and/or temperatures and tested at specified pressures and/or temperatures in the test vessel 124. Tensioning device 126 can be used to apply tension to a cement sample in test vessel 124 in the course of testing.

Controller 118 can be a manual or automatic controller. In some instances, a programmable automatic controller 118 can monitor temperature and pressure conditions in test vessel 124 based on data from thermocouple 128 and pressure source 116 and adjust temperature and pressure conditions in the test vessel 124 by sending appropriate control signals to temperature source 114 and pressure source 116. For example, temperature source 114 (e.g., an external heating jacket, cooling jacket, heat pump, heat exchanger, or other device) can be used to raise the temperature of test vessel 124 and pressure source 116 (e.g., a pumping system used to introduce a pressurizing fluid (discussed below) into the test vessel 124 or other device) can be used to raise the pressure present in the test vessel 124. Similarly, controller 118 can provide control signals to tensioning device 126 to operate the tensioning device during testing a cement sample and monitor data from the tensioning device and sensors (not shown) in test vessel 124 to gather the data necessary for calculation of mechanical properties. The calculation of mechanical properties based on the measured data can be performed by controller 118 or in a separate device/program.

In certain embodiments, the specified temperature and/or pressure conditions noted above can be above or below ambient temperature, above or below ambient pressure, and in some instances can be selected to simulate downhole pressure and/or temperature. The specified temperature and/or pressure can be different for different portions of the system 100 or a different times during the operation of the system 100. For example, the temperature and/or pressure in the cement source 112 (conditioner 120 or mixer 122) may be different from the temperature and/or pressure in the test vessel 124. In some instances the temperature and/or pressure in mixer 122 can be different than temperature and/or pressure in the conditioner 120. In certain instances, the temperature and/or pressure applied to the cement as it is received in the test vessel 124 can be different than during curing and/or testing the cement. In certain instances, the specified temperature and/or pressure applied during the curing is the same or may be different as that applied during testing.

The temperatures and/or pressures can be specified to simulate pumping placement conditions and/or static well bore conditions. For example, in certain instances, it may be desirable to simulate anticipated pumping placement conditions the cement will be subjected to in use, while the cement is in the conditioner 120. In certain instances, it may be desirable to simulate anticipated static well bore conditions the cement will be subjected to in use, while the cement is curing and being tested in the test vessel 124. Static well bore conditions are the temperature and pressure the cement is subjected to once substantially in place in the well bore. Pumping placement conditions are the temperature and pressure the cement is subjected to while being pumped down the well bore and into place. Typical static downhole pressures can range from below 0 MPa to above 20 MPa, and typical downhole temperatures can range from 65° Celsius to above 250° Celsius; however, in some instances they are below 1° Celsius. The anticipated conditions (pumping placement, static or otherwise) can be determined in a number of ways. For example, the anticipated conditions may be based on specifications of conditions provided by a purchaser of the cement or cementing services, substantially matched to conditions measured or calculated from one or more drilled or partially drilled wells (including the well the cement will be used in, similarly configured wells in the same field, and/or other wells), and/or derived from design conditions determined for desired future use.

Figure 2:
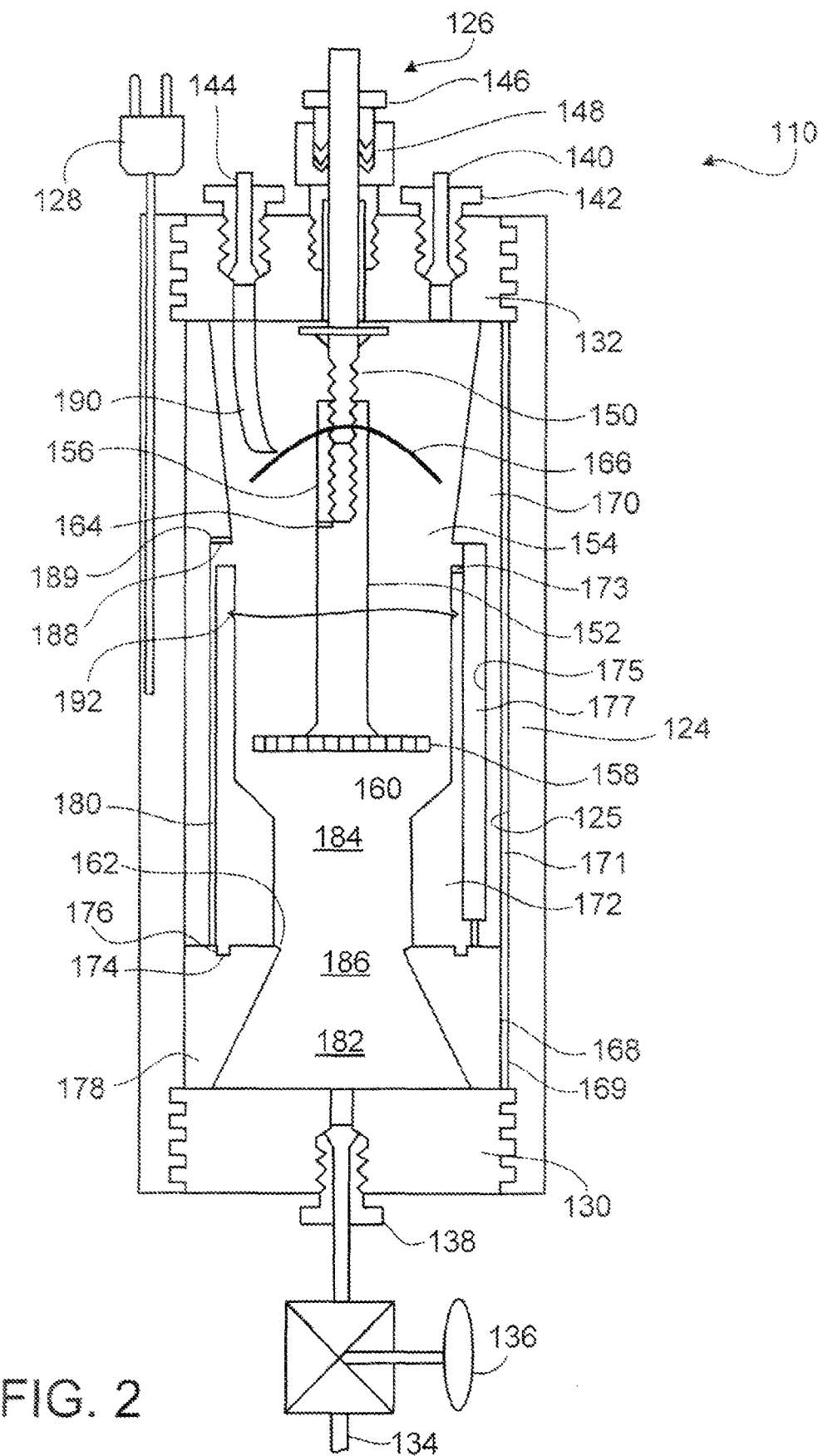
FIG. 2 is a cross-sectional view of an embodiment of a testing device that can be used with the system of FIG. 1.

Cement introduced from the cement source 112 (FIG. 1) into test vessel 124 can be maintained at specified temperature and/or pressure without exposing the cement to ambient conditions (if ambient conditions are not the specified pressure and temperature). Referring to FIG. 2, in some embodiments, test vessel 124 includes a first end cap 130 and a second end cap 132. Test vessel 124 can receive a high pressure line 134 having a valve 136 through which cement can flow from the cement source 112 while maintaining the cement at specified temperature and/or pressure. In some instances, high pressure line 134 can be insulated to help maintain temperature of the cement therein. First end cap 130 has an aperture receiving a plug 138 sized to accept high pressure line 134. In other embodiments, i.e. embodiments omitting high pressure line 134, fluid cement can be introduced into test vessel 124 by methods including, for example, pouring unconditioned cement or conditioned cement into the test vessel 124. In such embodiments, the first end cap 130 can be sealed with a solid plug (not shown) or the first end cap can be formed without an aperture.

The test vessel 124 can have a second end cap 132. In some instances, the second end cap 132 includes a vent with a vent plug 140 and vent nut 142 and a fill port 144. A load shaft 156 can extend through the second end cap 132 with a packing nut 146 and packing 148 (e.g. chevron packing) providing a pressure-tight seal. Loads can be applied to cement in testing device 110 via the load shaft 156 using a variety of mechanisms. For example, testing device 110 can include a rotating device (e.g., a Servodyne™ motor sold by Cole Parmer Instrument Company) or other mechanism, electrical, hydraulic, mechanical or other, that can turn a first portion 150 of load shaft 156. In this embodiment, the first portion 150 and second portion 152 are coupled by threads that constitute a gear drive translating rotational movement the first portion 150 to axial movement of the second portion 152. An axial load on cement fixed to the second portion 152 of the load shaft 156 can be applied by rotating the first portion 150. Alternatively, testing device 110 can include a linear loading device driven by electrical, hydraulic, or mechanical means (e.g., a testing load frame such as a Super "L" Universal Testing Machines™ sold by Tinius Olsen Testing Machine Co.) configured to directly pull on load shaft 156, thus creating a tensile load on cement fixed to the second portion 152 of the load shaft 156. In either instance, loads applied by a rotating device or a linear device, the cement can be tensile tested by applying a tensile load to the cement and measuring one or more of the magnitude of the tensile load applied, the rate at which the load is applied, the amount of elongation of the cement. In certain embodiments, the load may be applied all at once or in one or more stages. In certain embodiments, the rate of elongation can be constant and the load measured. From the information obtained from the tensile test and dimensional measurements of the cement sample, mechanical properties such as tensile strength, Poisson's ratio, Young's modulus and other properties can be calculated.

In some embodiments, first portion 150 of load shaft 156 can extend through first end cap 132 into a cavity 154. An anchor member 158 can be mounted on an end of second portion 152 of load shaft 156 to provide engagement between the load shaft and cement curing or cured around the anchor member and the load shaft. For example, in some instances, anchor member 158 can be a perforated plate welded onto the end of second portion 152. Perforated plate can have perforations 160 whose total cross-sectional area is substantially greater than the cross-sectional area of the desired break area 162, so as to prevent breakage of the cement at the cross-section of the plate. Second portion 152 of load shaft 156 can include a thread vent 164 to prevent a hydraulic lock or otherwise create excessive resistance in the apparatus which may impart error in torque readings.

A baffle 166 can be mounted on load shaft 156 such that the baffle is interposed between fill port 144 and anchor member 158. Baffle 166 can be configured to deflect fluids introduced via fill port 144, for example, to protect cement present in cavity 154 from contamination and/or disturbance as cement or other fluids are introduced into testing vessel 124.

In some embodiments, an interior wall of the test vessel 124 can be defined by one or more sleeves. For example, a first sleeve 168, second sleeve 170, and intermediate sleeve 172 can cooperate to substantially define the geometry of cavity 154. Alternatively, the interior test vessel 124 can be formed or machined with projections that define the cavity 154 geometry. First sleeve 168 and second sleeve 170 can be affixed in the cavity 154, for example, mounted on or attached to interior walls of test vessel 124 or to the first end cap 130. In certain embodiments, the first sleeve 168 and second sleeve 170 can be provided with respective keys 169, 171 received in a keyway 125 of the test vessel 124. The keys 169, 171 and keyway 125 cooperate to anchor the first sleeve 168 and second sleeve 170 against rotation relative to the test vessel 124. First sleeve 168 can taper inwards defining a broad cross-sectional area 178 adjacent end cap 132 to a narrower cross-sectional area (i.e. neck) portion defining a desired break area 162. Desired break area 162 is a portion of cavity 154 with reduced cross-sectional area relative to the rest of the cavity. The reduced cross-sectional area and associated reduced strength of the cement sample in this area are intended to cause the cement sample to fail in this specific location during tensile strength testing. A groove 174 can be machined in a face of first sleeve 168. Groove 174 can receive a corresponding ridge 176 in intermediate sleeve 172. The resulting engagement between first sleeve 168 and intermediate sleeve 172 can locate the intermediate sleeve relative to first sleeve 168 and can also serve as a low-pressure seal to limit passage of cement from between the sleeves into an annular gap 180 defined between the intermediate sleeve and second sleeve 170. In some instances, an O-ring and/or grease may be used to improve the seal formed by engagement between the first sleeve 168 and intermediate sleeve 172.

First sleeve 168 and intermediate sleeve 172 together define a lower cavity section 182 and an upper cavity section 184 that are joined by a transition section 186 at desired break area 162. The tower cavity section 182 defines a substantially frustoconical volume. The upper cavity section 184 defines a substantially cylindrical volume. Second portion 152 of load shaft 156 and attached anchor member 158 can extend into lower cavity section 182. In some embodiments, first sleeve 168 can have a substantially annular configuration and rounded edges at the transition section 186. When lower cavity section 182, upper cavity section 184, and transition section 186 are filled with cement, the resulting cement sample has rounded surfaces at desired break area 162 thus avoiding sharp corners or geometry changes that may focus stress at specific locations in the sample.

Intermediate sleeve 172 may be constructed of carbon steel, aluminum, plastic, fiberglass, or resin-coated metals (e.g., material to which a shear bond test between the cement and subject metal is desired). The surface of sleeve 172 may also be affected by various finishes such as resins, mill varnish, sand blasting, or other means to affect the frictional properties of said sleeve as required by the application for which the test is being conducted. In some instances, the material and surface finish can be selected to simulate a well casing.

Second sleeve 170 extends from second end cap 132 to first sleeve 168. Where second sleeve 170 overlaps intermediate sleeve 172, the second sleeve has an inner diameter that exceeds an outer diameter of the intermediate sleeve and defines an annular gap 180. Second sleeve 170 can include a shoulder or intermediate sleeve stop 188. The intermediate sleeve stop 188 is spaced from the end of first sleeve 168 by a distance greater than the length of the intermediate sleeve 172, allowing the intermediate sleeve 172 to translate axially within the test vessel 124 a specified distance. In certain embodiments, the intermediate sleeve 172 can be anchored against rotation relative to the second sleeve 170 when abutting the second sleeve 170. For example, an end face of intermediate sleeve 172 can include teeth 173 configured to mesh with corresponding teeth 189 on the intermediate sleeve stop 188 when the intermediate sleeve 172 abuts the sleeve stop 188. When meshed, the teeth 173, 189 cooperate to anchor the intermediate sleeve 172 against rotation relative to the second sleeve 170 and test vessel 124. In certain embodiments, in addition to or as an alternative to teeth 173, 189, intermediate sleeve 172 can be anchored against rotation relative to the second sleeve 170 and test vessel 124 using a key 177 residing in a key way 175 defined by the intermediate sleeve 172 and second sleeve 170. When engaged, the key 177 and keyway 175 cooperate to anchor the intermediate sleeve 172 against rotation relative to the second sleeve 170 and the test vessel 124, but allow axial translation of the intermediate sleeve in the test vessel 124. Although only one key 177 and keyway 175 are shown, certain embodiments may have multiple keys 177 and keyways 175. For example, in one instance, two sets of key 177 and keyway 175 are provided, diametrically opposed about the intermediate sleeve 172.

In some embodiments, a piece of flexible tube 190 can extend from fill port 144 into cavity 154. The flexible tube 190 may be provided entirely above the baffle 166 or may extend to about the fill line 192, for example, by being inserted through a hole or slot in a baffle 166.

In some embodiments, testing device 110 can include sensors (not shown) such as strain gauges that would allow the tensile modulus and tensile Poisson ratio of the cement sample to be determined as the tensile load is applied. In some embodiments the sensors can be cast in the cement, affixed to components of or a wall of the test vessel 124, or other.

Testing device 110 can include a thermocouple 128 for monitoring temperature of the testing device. In some embodiments, thermocouple 128 is located in a wall of test vessel 124.

Figure 3:
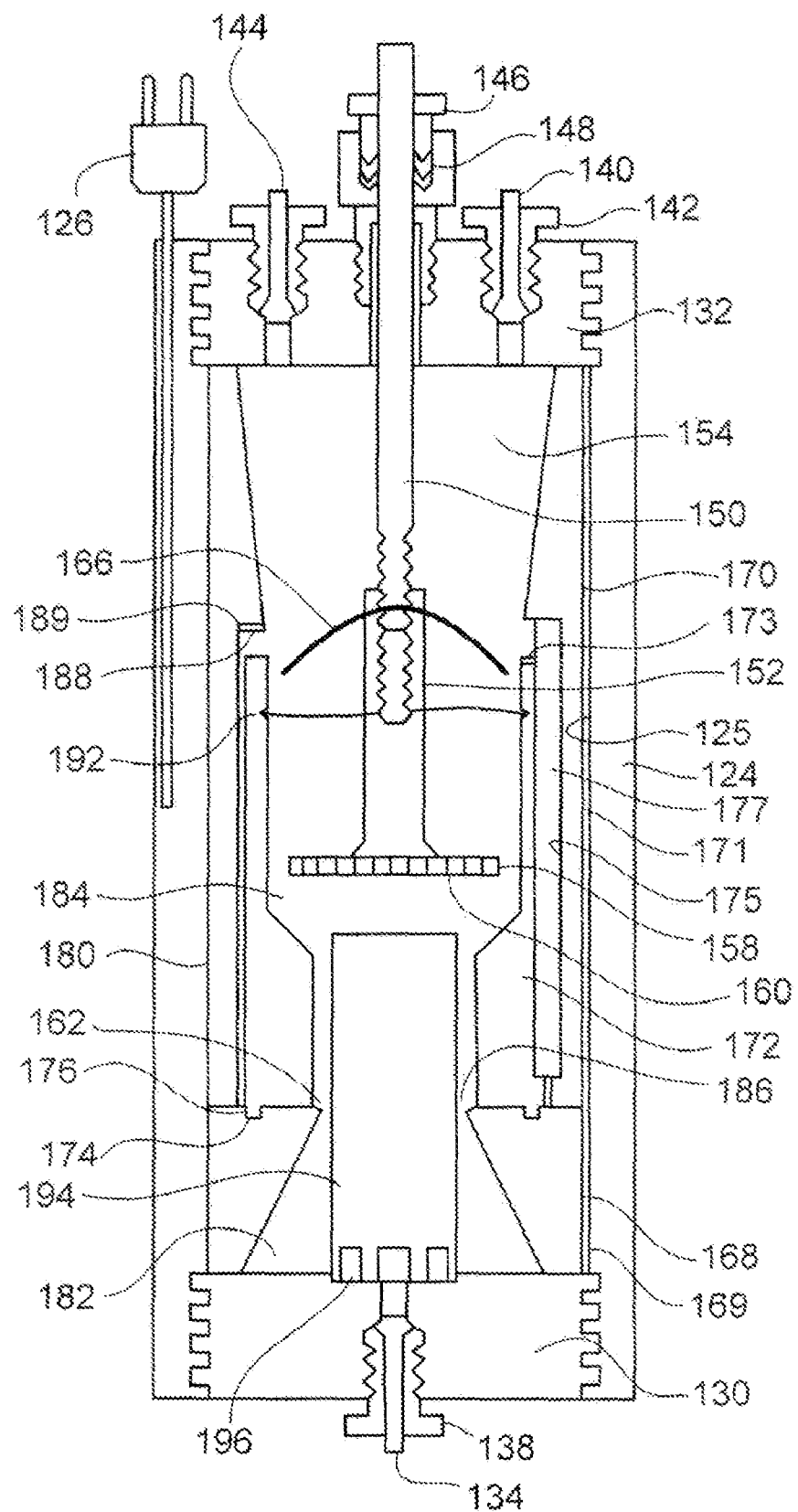
FIG. 3 is a cross-sectional view of another embodiment of a testing device that can be used with the system of FIG. 1.

Referring to FIG. 3, in some embodiments, testing device 110 can also include insert 194. In certain embodiments, the insert 194 can be made of a material that the cement would not bond to and/or the insert can be lightly greased. In certain embodiments, the insert 194 can be flexible, for example, constructed from soft rubber, plastic, or other readily flexible material. In one instance, the insert 194 is a hollow rubber bladder filled with liquid (e.g. water). The insert 194 displaces cement from the interior of the cavity 154 in order to cause the cement to cure in an annular shape at the break area 162, i.e. similar to the annular shape of the cement when formed between a casing and the wall of a well bore. Insert 194 can be mounted over the aperture in first end cap 132 and can include slurry fill slots 196 through which the cement can be introduced into cavity 154.

Various methods of testing can be implemented using the devices and systems of FIGS. 1-3. These devices and systems enable the cement to be mixed, conditioned, cured and/or tested at specified (above/below/at ambient) temperature and/or specified (above/below/at ambient) pressure. Furthermore, the cement can be maintained at specified temperature and/or specified pressure when transferred from the mixer 122 (if provided) to the conditioner 120 and from the conditioner 120 to the test vessel 124. The temperature and/or pressure can be different in different stages of the system. For example, the cement may be mixed at one temperature, further conditioned at another temperature, and cured and tested at yet another temperature. Likewise, the cement may be mixed at one pressure, further conditioned at another pressure, and cured and tested at yet another pressure. Moreover, the temperature and/or pressure can be varied during a given stage of the system. For example, the cement may be initially conditioned at one temperature and pressure and subsequently conditioned at a different temperature and/or pressure. One will appreciate that numerous combinations of pressure and temperature in various stages of the system (mixing, conditioning, curing and testing) can be achieved.

Referring specifically to FIGS. 1 and 2, in one embodiment, a method of testing mechanical properties of cement includes mixing, curing and testing the cement at elevated (above ambient) pressures and temperatures selected to simulate downhole conditions. According to the method, the cement is mixed in the mixer 122 at a temperature and a pressure elevated above ambient conditions and transferred to the conditioner 120 at the temperature and pressure. The cement is then introduced into the test vessel 124 in which the temperature and pressure have been increased above ambient conditions in order to simulate several conditions. In some instances, test vessel 124 can be temperature controlled using external temperature source 114 controlled either manually or automatically in response to temperatures measured by thermocouple 128. An external pressure source 116 can be connected to fill port 144 and used to fill test vessel 124 with a pressurizing fluid (e.g., water, brine, oil, or a gas such as nitrogen). The pressurizing fluid effectively displaces volume within the test vessel 124 available for cement. As such, the pressure and volume of the pressurizing fluid in the test vessel 124 can be regulated to exert or maintain a pressure on, i.e. control the pressure of, the cement in the test vessel 124. In other embodiments, a piston, expandable bladder, movable walls in the test vessel 124, or other apparatus (not specifically shown) can be used to exert or maintain pressure on, and control the pressure of, the cement in the test vessel 124.

In some instances, pressure can be monitored via fill port 144 and vent tube 190 and temperature can be maintained via external heating jacket with both the external pressure source and the external heating jacket, both controlled by a microprocessor that monitors temperature thermocouple 128 and pressure sensors. Alternately, the temperature and/or pressure can be controlled manually.

Cement is introduced into test vessel 124 through high pressure line 134 which extends between the conditioner 120 and test vessel 124. Before filling begins, intermediate sleeve 172 can be set in engagement with first sleeve 168.

After equalizing pressure in the conditioner 120 and the test vessel 124, high pressure valve 136 can be opened permitting fluid communication between the conditioning device and the test vessel 124. Because a pressurizing fluid and the cement are under substantially equal pressures, little or no relative motion occurs. The cement can be introduced into test vessel 124 by opening vent plug 140 and, thus, allowing the pressurizing fluid to leave the test vessel 124 while the cement is introduced. By controlling the extent to which vent plug 140 is opened, the pressure in test vessel 124 can be maintained at or near a desired pressure. During operation, the testing device will be placed in an upright position such that lower cavity section 182 of cavity 154 is vertically below second section 184 of cavity 154. Thus, as the cement is introduced into the chamber, it can fill the void space defined by first sleeve 168 and intermediate sleeve 172 until it reaches a desired level in the test chamber.

In some instances (e.g., when filling test vessel 124 from the bottom with a fluid such as a foamed cement), flexible tube 190 can extend to desired fill line 192 and is used to pass excess slurry out of the chamber so as to prevent over-filling intermediate sleeve 172 and allowing cement into gap 180. As noted above, flexible tube 190 can extend through a hole or slot in baffle 166 or, in some instances, the baffle can be removed from test vessel 124.

Annular gap 180 between second sleeve 170 and intermediate sleeve 172 retains pressurizing fluid so that the pressurizing fluid can provide substantially even transmission of heat to the intermediate sleeve and can limit friction forces when the intermediate sleeve moves axially during testing. As discussed above, engagement between first sleeve 168 and intermediate sleeve 172 can act to limit passage of cement into gap 180 and pressurizing fluid from gap 180 into the cement.

When test vessel 124 is filled to the desired extent with the cement, high pressure valve 136, fill port 144, and vent plug 140 are closed. The cement surrounds perforated anchor member 158 and partially up first load shaft portion 150. Thereafter, cement in testing device 110 cures. By regulating the pressure and temperature of the cavity 154, the cement can cure under temperature and pressure conditions that simulate downhole conditions.

As discussed above with reference to FIG. 3, in some embodiments, insert 194 can be placed in testing device 110 to form the cement in an annular shape about the desired break area 162.

In embodiments where the high pressure line 134 is not used in conveying cement into the test vessel 124 or embodiments omitting high pressure line 134, cement can be introduced into test vessel 124 by methods including, for example, pouring unconditioned or conditioned fluid cement directly into the test vessel 124. The cement can be introduced through fill port 144 and may be directed into intermediate sleeve 172 using flexible tube 190. In such embodiments, a pressurizing fluid (e.g., water, brine, oil, or a gas such as nitrogen) can be added to test vessel 124 after the cement sample is in place. Baffle 166 protects the slurry from contamination/disturbance as the pressurizing fluid is introduced. Thus, the cement sample can initially be under ambient conditions before temperature and pressure conditions are adjusted as previously described. The cement can then be allowed to cure inside the chamber at specified pressure and temperature until such time that the actual testing is performed.

In some instances, testing (e.g., by applying tension to the cement) can be performed before curing is complete (i.e., before the cement is completely solidified). Such testing can provide useful information about the mechanical properties a particular cement possess if the cement is subjected to stresses (e.g., downhole stresses due to continuing drilling operations) before the cement has completely solidified. In other instances, testing can be performed after curing is complete.

One manner of testing mechanical properties of the cement is by applying tension to the cement. As discussed above, a motor can rotate first portion 150 of load shaft 156 to induce an axial upward motion in second portion 152 of the load shaft. As upward force is applied to second portion 152 of load shaft 156 and anchor member 158, the cement sample is held in place by first sleeve 168 from the bottom, thus creating a tensile load in the cement sample.

When sufficient axial force is applied to the cement sample, the cement sample breaks at the break area 162 in the transition section 186 of cavity 154 because of the reduced cross-sectional area of the cement sample at break area 162. The tensile load that is being applied to the sample at the point of failure can be calculated from measurements of the torque applied to the first portion 150. In one instance, the torque is recorded by controller 118. The recorded torque can then be used to calculate the tensile strength of the cement (e.g., by the controller software or by the user in a separate program). As discussed above, thread vent 164 in second shaft portion 152 exists so as to prevent a hydraulic lock or otherwise create excessive resistance in the apparatus which may impart error in the torque readings. Alternately, or in combination with measuring torque, sensors cast into the cement sample (not shown) or in the testing device 110 can measure the tensile load on the cement sample. The axial strain of the cement sample can be calculated from the angular displacement of the first portion 150 and/or by sensors. In one instance, the angular displacement of the first portion 150 is recorded by controller 118. If sensors are used, the output from the sensors can likewise be recorded by controller 118. Using the information obtained from the tensile test, mechanical properties including Young's modulus, Poisson's ratio, tensile strength, and others can be determined.

After the cement sample breaks, intermediate sleeve 172 and an upper portion of the sample move upward in response to the continuing application of force through load shaft 156 until intermediate sleeve 172 engages second sleeve 170. Between breaking of the cement sample and this engagement, intermediate sleeve 172 and the contained portion of the cement sample travel upwards relatively freely. The torque readings measured during this free-travel period can be used to calculate friction forces in the apparatus that may exist in the drive mechanisms. The calculated friction forces can be used to correct the readings obtained for the tensile test or for the shear bond test (described below).

After intermediate sleeve 172 engages second sleeve 170, a shear force develops between the now stationary portion of the cement sample held in sleeve 172 and the sleeve 172. The force can be increased until the shear bond holding the cement sample to the intermediate sleeve 172 fails. The torque or load recorded at this point of failure can then used to calculate the shear bond strength between the cement and the sleeve 172.

Although described above as used in applying a tensile force across the cement sample, the assembly of shaft 156 can be used to impart compressional loads to the sample. Such compression loading, in some instances, can enable determination of compressional Young's modulus, Poisson's ratio, and used in other analysis.

A number of embodiments have been described. Nevertheless, it will be understood that various modifications may be made without departing from the concepts described herein. Accordingly, other embodiments are within the scope of the following claims.

What is claimed is:

1. A method, comprising:
    conditioning cement in a conditioning vessel;
    receiving the cement in a testing vessel, the cement curing in the testing vessel;
    testing a mechanical property of the cement in a testing vessel, the cement conditioned, cured and tested while applying a specified temperature and/or pressure;
    wherein testing a mechanical property of the cement comprises testing a shear bond strength of the cement; and
    loading the cement in tension until the cement breaks before testing the shear bond strength of the cement.

2. The method of claim 1 wherein the specified temperature and/or pressure applied while testing and curing substantially simulates anticipated static downhole conditions the cement will be subjected to in use.

3. The method of claim 1 wherein the specified temperature and/or pressure applied while conditioning substantially simulates pumping placement conditions the cement will be subjected to in use.

4. The method of claim 1 further comprising receiving the cement in the testing vessel while applying specified temperature and/or pressure to the cement.

5. The method of claim 4 wherein the specified temperature and/or pressure applied while receiving substantially simulates anticipated pumping placement conditions the cement will be subjected to in use.

6. The method of claim 1 wherein conditioning the cement comprises mixing the cement.

7. The method of claim 1 wherein testing a mechanical property of the cement comprises tensile testing the cement.

8. A system for testing cement, comprising:
    a testing vessel having interior walls defining a mold cavity to receive the cement; and
    a body in the mold cavity adapted to apply a specified pressure to the cement while it is being received in the mold cavity;

a load arm operable to load the cement in tension until a bond between the cement and the interior walls fails;

the load arm adapted to contact the cement and apply a testing load to the cement, the interior walls of the testing vessel configured to anchor the cement against the testing loads;

the load arm operable to load the cement in tension until failure at a break area; and wherein the testing vessel is adapted to mold the cement in an annular shape about the break area.

9. The system of claim 8 wherein the interior walls define at least a portion of the mold cavity as frustoconical.

10. The system of claim 9 wherein the interior walls define at least a portion of the mold cavity as cylindrical.

11. The system of claim 8 wherein the body is adapted to apply a specified pressure to the cement while the cement cures and while a mechanical property of the cement is being tested.

12. The system of claim 8 wherein the load arm is at least partially within the mold cavity so the cement cures around the load arm.

13. The system of claim 8 wherein the body is a fluid that is at least partially displaced as the cement is receive into the testing vessel.

14. The system of claim 8 further comprising a temperature source adapted to apply specified temperature to the cement in the testing vessel.

15. A method for testing cement, comprising:
receiving a cement in a testing vessel, the cement curing in the testing vessel;
testing a shear bond strength of the cement, the cement cured and tested while applying a specified temperature and/or pressure; and
loading the cement in tension until the cement breaks before testing the shear bond strength of the cement.

16. The method of claim 15 wherein the specified temperature and/or pressure applied while curing and testing substantially simulates anticipated static downhole conditions the cement will be subjected to in use.

17. A system for testing cement, comprising:
a testing vessel having interior walls defining a mold cavity to receive the cement; and
a body in the mold cavity adapted to apply a specified pressure to the cement while it is being received in the mold cavity; and
a load arm operable to load the cement in tension until a bond between the cement and the interior walls fails,
wherein the load arm is adapted to contact the cement and apply a testing load to load the cement in tension until failure at a break area; and
wherein the interior walls of the testing vessel are configured to anchor the cement against the testing loads and the testing vessel is adapted to mold the cement in an annular shape about the break area.

18. The system of claim 17 wherein the interior walls define at least a portion of the mold cavity as frustoconical.

19. The system of claim 18 wherein the interior walls define at least a portion of the mold cavity as cylindrical.

20. The system of claim 17 wherein the body is adapted to apply a specified pressure to the cement while the cement cures and while a mechanical property of the cement is being tested.

21. The system of claim 17 wherein the load arm is at least partially within the mold cavity so the cement cures around the load arm.

22. The system of claim 17 wherein the body is a fluid that is at least partially displaced as the cement is receive into the testing vessel.

23. The system of claim 17 further comprising a temperature source adapted to apply a specified temperature to the cement in the testing vessel.

* * * * *